US00PP10416P

United States Patent [19]

Jessel, Jr.

[11] Patent Number: Plant 10,416

[45] Date of Patent: May 26, 1998

[54] CARNATION PLANT NAMED 'CFPC PASSION'

[75] Inventor: Walter H. Jessel, Jr., Gonzales, Calif.

[73] Assignee: California Florida Plant Co., L.P., Salinas, Calif.

[21] Appl. No.: 749,921

[22] Filed: Nov. 12, 1996

[51] Int. Cl.[6] ..... A01H 5/00

[52] U.S. Cl. ..... Plt./70.2

[58] Field of Search ..... Plt./70.2, 70.6

*Primary Examiner*—Howard J. Locker

*Attorney, Agent, or Firm*—Christie, Parker & Hale, LLP

[57] ABSTRACT

A new plant variety of carnation plant producing sprays of purple flowers.

1 Drawing Sheet

BACKGROUND OF THE INVENTION

The present invention relates to a new and distinct variety of carnation plant which was discovered as a sport in a controlled planting of the cultivar 'CFPC Dream' (U.S. Plant Pat. application Ser. No. 08/749,920). The sport was found as 4 of 7 breaks on a plant of 'CFPC Dream', the remaining 3 shoots were the original 'CFPC Dream'. The varietal denomination of this new carnation is 'CFPC Passion'.

SUMMARY OF THE INVENTION

The new variety is a true dwarf carnation suitable for growing in 4 to 4½-inch pots (1 plant, 1 pinch i.e. 1 plant per pot with a single tip pinch), tolerant to temperatures of about 10 to 120° F. with a keeping quality of about 3 to 4 weeks. Flower buds open from green bud to maturity with moderate light. No disease problems have been observed as yet.

If planted outdoors, the new variety will continue to recycle growth and blooms. It appears to be perennial in nature in most sections of the country.

In addition to the foregoing, the new variety exhibits superior resistance to soil borne diseases such as *F. oxysporum*, strains 1 and 2, and *F. graminearum*, and root-rots such as damping off, water molds, and the like.

Asexual reproduction by propagation by side shoot cuttings of the new variety as performed in Salinas, Calif., shows that the foregoing and other distinguishing characteristics come true to form and are established and transmitted through succeeding propagations.

Comparison with parent

The flower color of 'CFPC Passion' differs in flower color inasmuch as flowers are solid red-purple.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Color Chart (RHSCC). The terminology used in color description herein refers to plate numbers in the aforementioned color chart. Phenotypic expression and color descriptions may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Passion'.

Classification:

*Botanical.*—*Dianthus caryophyllus.*

*Commercial.*—Carnation, greenhouse type, suitable as a pot variety producing flower sprays.

Parentage: Sport of 'CFPC Dream.'

1. Plant:
   - *Height.*—Pinched plants are about 7–9 inches tall.
   - *Growing habit.*—Herbaceous, semi-upright.
   - *Blooming habit.*—As a pot spray.
   - *Blooming season.*—Year round.
   - *Rooting time.*—About 17 days.
   - *Mutation prone.*—No.
   - *Disease resistance.*—Good.
   - *Temperature tolerance.*—Wide range.
   - *Breaking action.*—Very Good to excellent, average 7 to 8 lateral branches.
2. Foliage:
   - *Color.*—Upper side: Near 139B. Lower side: Near 138A.
   - *Size.*—About 3⅞ inches long, about ¼ inches wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem Color.*—Near 137A.
3. Bud:
   - *Shape.*—Ovoid.
   - *Color.*—Near 137B.
   - *Length.*—About 1 inch.
   - *Diameter.*—About ⅜ inch.
4. Calyx:
   - *Number of sepals.*—About 5.
   - *Length.*—About ½ inch.
   - *Width.*—About 3/16 inch.
   - *Color.*—Outside—Near 144A Inside—Near 143C.
5. Bloom:
   - *Shape.*—Round.
   - *Size.*—Diameter average: About 1¾ inches. Depth average: About ⅞ inch.

*Borne.*—As a spray, approximately 6 to 8 blooms per flowering stem, stem length about 7½ to 8½ inches.

*Color.*—General tonality: Purple-red. Upper side: Near 67A. Lower side: Near 67C. Center: Near 67A. Outer petals: Near 67A.

*Keeping quality.* About 3 weeks, flowers dry up on plant and do not drop.

*Fragrance.*—Slight to none.

6. Petals:

*Number.*—About 20.

*Outer petals.*—Length; About 1½ inches. Width: About ¾ inch.

*Central petals.*—Length: About 1⅜ inches. Width: About ½ inch.

*Texture.*—Smooth.

*Form.*—Fan shaped.

*Appearance.*—Shiny, petal margin is smooth.

7. Reproductive organs:

*Stamens.*—None (male sterile).

*Pistil.*—Number: About 1. Color: Whiter than 155D. Length: About 1 inch.

*Stigma.*—Number: About 2. Color: Near 186D.

*Ovary.*—Shape: Conical. Color: Base—Near 154C. Body—Near 145B. Apex—Near 19D.

*Fertility.*—Female: Good. Male: Sterile.

I claim:

1. A new and distinct variety of carnation plant substantially as shown and described.

* * * * *

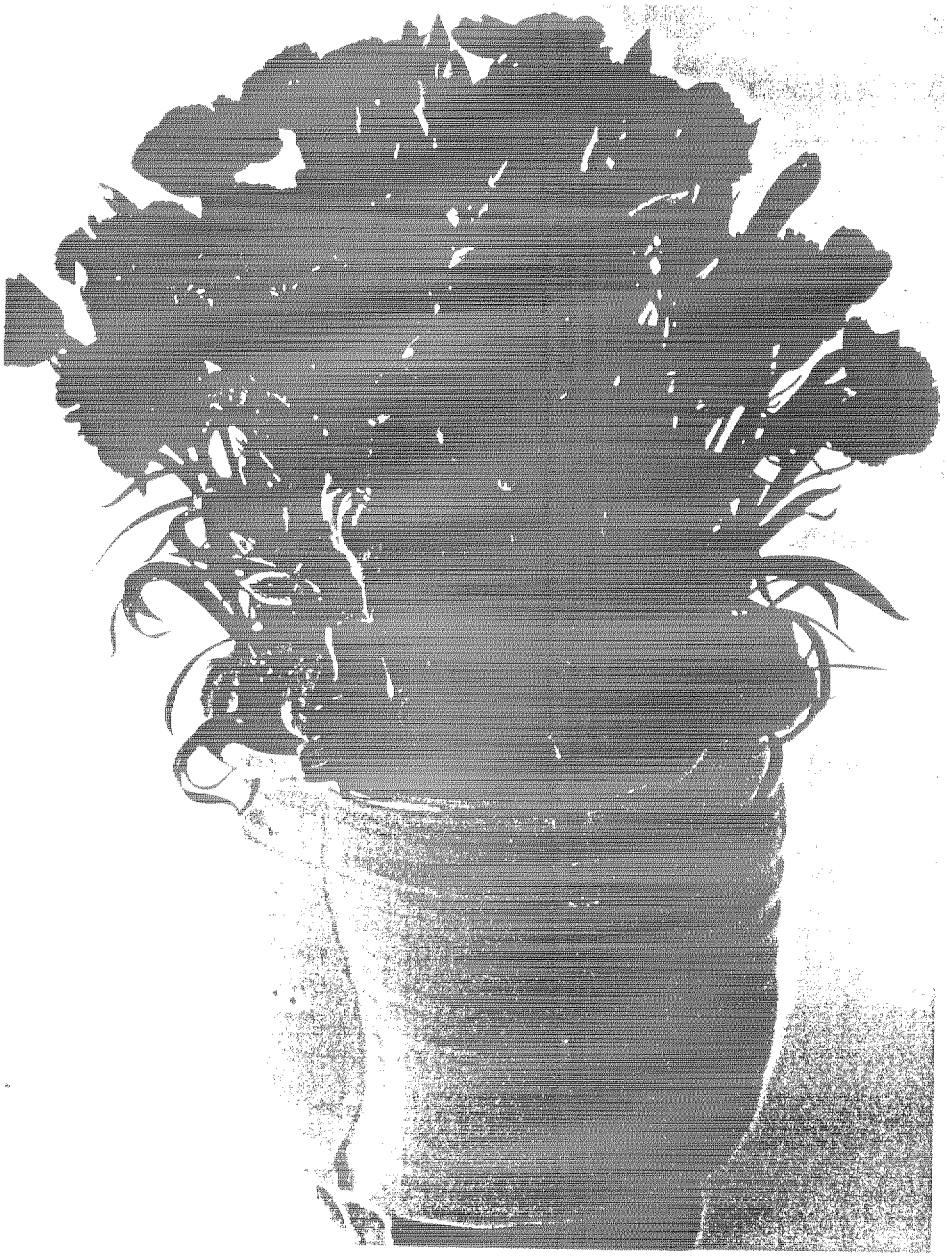

PLT-273 SR
C5203 OR PP 010,416
U.S. Patent May 26, 1998 Plant 10,416